United States Patent [19]

Tassara et al.

[11] Patent Number: 5,672,792
[45] Date of Patent: Sep. 30, 1997

[54] PROCESS FOR PREPARING CHLOROPRENE

[75] Inventors: Jean-Pierre Tassara, Villeurbanne; Michel Baudouin, Saint Genis les Olliéres, both of France

[73] Assignee: Enichem Elastomeres France SA, Courbevoie, France

[21] Appl. No.: 308,307

[22] Filed: Sep. 19, 1994

[30] Foreign Application Priority Data

Sep. 17, 1993 [FR] France ................... 93 11303

[51] Int. Cl.$^6$ ............................. C07C 17/25; C07C 21/21
[52] U.S. Cl. .................................................. 570/229
[58] Field of Search .......................... 570/227–228, 570/229

[56] References Cited

U.S. PATENT DOCUMENTS

| | | | |
|---|---|---|---|
| 2,291,375 | 7/1942 | Cass | 570/229 |
| 2,322,258 | 6/1943 | Strosacker et al. | 570/228 |
| 2,598,646 | 5/1952 | Maude et al. | 570/229 |
| 3,079,446 | 2/1963 | MacFarlane | 570/229 |
| 3,755,476 | 8/1973 | Crary et al. | 570/228 |
| 3,936,508 | 2/1976 | Wenzel et al. | 570/229 |

FOREIGN PATENT DOCUMENTS 231886  7/1944  Switzerland.

OTHER PUBLICATIONS

Patent Abstract of Japanese Patent No. 56156223 (Feb. 12, 1981).

*Primary Examiner*—Richard D. Lovering
*Attorney, Agent, or Firm*—Burns, Doane, Swecker & Mathis, L.L.P.

[57] ABSTRACT

Process for preparing chloroprene by dehydrochlorinating 3,4-dichloro-1-butene in the presence of lime and a polyol, such as a glycol selected from (poly)ethylene glycol and (poly)propylene glycol or sugars, with ethylene glycol being preferred.

6 Claims, No Drawings

PROCESS FOR PREPARING CHLOROPRENE

The present invention relates to a process for preparing 2-chlorobutadiene-1,3 ("chloroprene") by means of the dehydrochlorination of 3,4-dichloro-1-butene (DCB) and, in particular, to a process for preparing chloroprene by starting from DCB, in which DCB is dehydrochlorinated with lime.

The present process for preparing chloroprene consists in dehydrochlorinating DCB with sodium hydroxide. The consumption of sodium hydroxide is stoichiometric, and, consequently, the cost thereof strongly increases the total process costs.

Therefore, attempts were carried out in the past in order to develop less expensive solutions than using sodium hydroxide. In particular, the replacement of sodium hydroxide with less expensive lime was proposed. The problem which had to be solved in this case, derives from low lime reactivity.

Some DCB dehydrochlorinating processes, using lime as the basic reactant, are disclosed in some patent references.

So, e.g., JP-51/43 705 discloses a system constituted by calcium hydroxide and sodium sulfate. Said process is schematically represented by the equation:

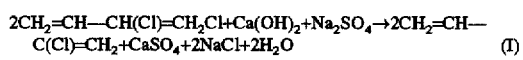

$$2CH_2=CH-CH(Cl)-CH_2Cl+Ca(OH)_2+Na_2SO_4 \rightarrow 2CH_2=CH-C(Cl)=CH_2+CaSO_4+2NaCl+2H_2O \quad (I)$$

The main drawback displayed by this process consists in that two byproducts are produced, and namely, calcium sulfate and sodium chloride.

In particular, $CaSO_4$, insoluble in water, should be separated from the aqueous solution which contains sodium chloride. This step adds up to the costs of the overall process. Furthermore, the process disclosed in this patent does not allow a quantitative conversion to be obtained.

This being the state of the art, the present Applicant was able to develop a process for dehydrochlorinating DCB into chloroprene, which overcomes the above drawbacks.

In accordance with the above, the present invention relates to a process for preparing chloroprene by means of 3,4-dichloro-1-butene dehydrochlorination, characterized in that said dehydrochlorination is carried out in the presence of lime and at least one glycol selected from the group consisting of (poly)ethylene glycol, (poly)propylene glycol, and/or at least one sugar, with ethylene glycol being particularly preferred.

By "lime", calcium oxide or calcium hydroxide or mixtures thereof, are meant herein.

By "(poly)glycol", ethylene glycol or propylene glycol, and their polymers are meant herein.

By "sugars", saccharose and its derivatives, i.e., mono-, oligo- or polysaccharides, which may be either hydrogenated or non-hydrogenated, and their analogues, are meant herein. As exemplifying sugars, glucose, sorbitol, glycerol, and so forth, are mentioned.

The reaction of dehydrochlorination is carried out at a temperature comprised within the range of from 70° to 150° C., preferably of from 80° to 120° C.

Preferably, the reaction temperature should neither be lower than the lower threshold value (too slow reaction kinetics), nor higher than the upper threshold value (faster polymerization).

According to a preferred embodiment, the reactor is charged with lime and glycol; the resulting mixture is then heated, with stirring, up to the desired temperature.

DCB is then added to the reactor by means of an addition funnel. DCB should preferably be added after a time period of from 10 to 60 minutes.

The dehydrochlorination is completed after a variable time period which is a function of the selected temperature, of the desired conversion rate and of glycol. For instance, in the presence of ethylene glycol at 100° C., in order to obtain a nearly quantitative DCB conversion, a 90-minute reaction time will suffice.

As it is progressively formed, chloroprene can be separated from the reaction mixture by distillation.

When reaction is complete, any formed chloroprene has been nearly totally collected. The contents of chloroprene and DCB in the residual mixture inside the reactor, are consequently very small.

Lime should be present in an amount of at least 0.5 mol of calcium per each DCB mol. However, a small excess of lime should preferably be used, preferably of from 0.51 to 1.5 mol of lime per mol of DCB.

When a glycol is used, the molar amount of alkyleneoxy moieties should be at least the same as of lime. According to preferred embodiment, glycol is also used as a solvent, hence in a large excess.

As regards polyglycols, they usually have a molecular weight comprised within the range of from 200 to 1000, preferably of from 300 to 800.

According to another embodiment, the reaction system can be diluted with water or an inert solvent, in particular an ethylene glycol ether.

At the end of the reaction, and of the distillation of formed chloroprene, the liquid residue contains the glycol and calcium chloride. Ethylene or propylene glycol can be recovered by distillation, whereas polyglycols can be recovered by extraction.

The following examples are supplied in order to illustrate the present invention in greater detail.

EXAMPLE 1

The process system consists of a glass reactor (of 200 cm³ of capacity), equipped with mechanical stirring means and oil-bath heating, a dropping funnel and an external vapour condenser.

The reactor is charged with 100 g (1.61 mol) of ethylene glycol and 10.4 g (0.14 mol) of $Ca(OH)_2$.

The mixture is stirred and heated up to 100° C.

From the dropping funnel, 31.25 g (0.25 mol) of 3,4-dichloro-1-butene (DCB) is added during 30 minutes.

The reaction mixture is kept at 100° C. with stirring for a further hour.

At this time, 18.5 g has been distilled and collected of a liquid, the gaschromatographic analysis of which shows that it contains 74% of chloroprene and 8% of dichlorobutene.

The analysis of the residual mixture in the reactor shows that it contains 1.48 g of chloroprene (DCB is no longer present).

The conversion of DCB is 95.2% and chloroprene yield 72% based reacted dichlorobutene.

EXAMPLE 2

According to the same process of Example 1, 0.25 mol of DCB, 0.25 mol of $Ca(OH)_2$ and 1.61 mol of ethylene glycol are used.

The conversion of DCB is 97.6% and chloroprene yield is 68.9% based on reacted dichlorobutene.

EXAMPLE 3

According to the same process of Example 1, 0.25 mol of DCB, 0.68 mol of ethoxyethanol, 0.24 mol of ethylene glycol and 0.14 mol of $Ca(OH)_2$ are used.

The conversion of DCB is 61.2% and chloroprene yield is 46.8%.

EXAMPLE 4

The test of Example 1 is repeated, with ethylene glycol being replaced by 100 g of polyethylene glycol with an average molecular weight of 300.

After a 4-hour reaction, 11.4 g were distilled of a mixture containing 86% of chloroprene and 3% of DCB.

The overall balance of the test shows that dichlorobutene conversion rate is 99.2% and chloroprene yields is 47%.

EXAMPLE 5

According to the same process of Example 1, 1 mol of DCB, 0.55 mol of $Ca(OH)_2$ and 4 mol of propylene glycol are used.

After a 90-minute reaction time at 81° C., the DCB conversion is 99% and chloroprene yield is 60%.

EXAMPLE 6

According to the same process of Example 1, 1 mol of DCB, 0.55 mol Of CaO and 1.8 mol of ethylene glycol are used.

After an 80-minute reaction time at 90° C., the DCB conversion is 100% and chloroprene yield is 24%.

COMPARISON EXAMPLE 7

According to the same process of Example 1, 0.25 mol of DCB, 0.76 mol of ethoxyethanol and 0.25 mol of $Ca(OH)_2$ are used.

After 4 hours at 102° C., the DCB conversion is 24% and chloroprene yield, based on used DCB, is lower than 2%.

COMPARISON EXAMPLE 8

According to the same process of Example 1, 0.25 mol of DCB, 0.14 mol Of $Ca(OH)_2$ and 4.97 mol of water are used.

After 4 hours at 92° C., the DCB conversion is 8% and chloroprene yield of 2%.

We claim:

1. A process for preparing chloroprene, said process comprising dehydrochlorinating 3,4-dichloro-1-butene in the presence of lime and at least one glycol selected from the group consisting of (poly)ethylene glycol, (poly)propylene glycol and sugars in a substantially non-aqueous medium.

2. The process according to claim 1, wherein said at least one glycol is ethylene glycol.

3. The process according to claim 1, wherein the dehydrochlorination step is carried out at a temperature between 70° and 150° C.

4. The process according to claim 3, wherein the hydrochlorination step is carried out at a temperature between 80° and 120° C.

5. The process according to claim 1, wherein said lime is present in an amount of at least 0.5 mol of calcium per mole of 3,4-dichloro-1-butene.

6. The process according to claim 5, wherein said lime is present in an amount between 0.51 and 1.5 mol of calcium per mole of 3,4-dichloro-1-butene.

\* \* \* \* \*